United States Patent
Barr et al.

(10) Patent No.: US 12,004,753 B2
(45) Date of Patent: Jun. 11, 2024

(54) TOURNIQUET ASSEMBLIES AND SYSTEMS, AND METHODS FOR CONTROLLING TOURNIQUETS

(71) Applicants: Martiurion Electronics Limited, Lisburn (GB); James S. Stewart, Baileyton, AL (US); Christopher Green, Moody, AL (US); Ashish Shah, Vestavia, AL (US)

(72) Inventors: Andrew Barr, Annahilt (GB); James S. Stewart, Baileyton, AL (US); Christopher Green, Moody, AL (US); Ashish Shah, Vestavia, AL (US)

(73) Assignee: Marturion Electronics Limited, Lisburn (GB)

( * ) Notice: Subject to any disclaimer, the term of this patent is extended or adjusted under 35 U.S.C. 154(b) by 0 days.

(21) Appl. No.: 17/492,076

(22) Filed: Oct. 1, 2021

(65) Prior Publication Data
US 2023/0107848 A1  Apr. 6, 2023

(51) Int. Cl.
| | | |
|---|---|---|
| *A61B 17/135* | (2006.01) |
| *A61B 5/022* | (2006.01) |
| *A61B 17/00* | (2006.01) |
| *A61B 17/132* | (2006.01) |
| *A61B 90/00* | (2016.01) |

(52) U.S. Cl.
CPC .......... *A61B 17/1355* (2013.01); *A61B 5/022* (2013.01); *A61B 5/02233* (2013.01); *A61B 2017/00022* (2013.01); *A61B 17/132* (2013.01); *A61B 17/135* (2013.01); *A61B 2090/063* (2016.02); *A61B 2562/0261* (2013.01)

(58) Field of Classification Search
CPC ... A61B 17/132; A61B 17/12; A61B 5/02233; A61B 17/1322; A61B 17/1325; A61B 17/1327; A61B 17/135; A61B 17/1355; A61B 17/32; A61B 5/68; A61B 5/6801; A61B 17/00; A61B 5/022; A61B 8/065; A61B 8/06; A61B 8/04; A61B 7/045; A61B 5/145; A61B 5/02007; A61F 5/34
USPC .................................................. 606/202, 203
See application file for complete search history.

(56) References Cited

U.S. PATENT DOCUMENTS

| | | | |
|---|---|---|---|
| 2002/0016610 A1* | 2/2002 | Hovanes ............ | A61B 17/1355 606/203 |
| 2007/0032819 A1* | 2/2007 | McEwen ............ | A61B 17/1322 606/202 |

(Continued)

*Primary Examiner* — Shaun L David
*Assistant Examiner* — Mitchell Brian Hoag
(74) *Attorney, Agent, or Firm* — Whiteford, Taylor & Preston, LLP; Gregory M. Stone

(57) ABSTRACT

A tourniquet for occluding blood flow to a limb is improved by the addition of proximal and distal strain gauges. The proximal strain gauge may be monitored under conditions of total blood flow occlusion for time-varying signals indicative of volumetric limb changes arising from the subject's blood flow in the proximal section of the limb. Upon a change in limb occlusion pressure, the signals from the proximal strain gauge can be observed to change also, and the working pressure in the tourniquet can be adjusted safely in response. Automated control systems may further use inputs from a distal strain gauge and/or from a sensor that detects induced pressure changes within the tourniquet to improve the control of the tourniquet working pressure during operation to avoid unwanted blood flow past the tourniquet.

6 Claims, 8 Drawing Sheets

(56) References Cited

U.S. PATENT DOCUMENTS

| | | | | |
|---|---|---|---|---|
| 2008/0262533 A1* | 10/2008 | McEwen | ............ | A61B 17/1355 |
| | | | | 606/202 |
| 2008/0281202 A1* | 11/2008 | Fraser | .................. | A61B 5/6843 |
| | | | | 601/3 |
| 2008/0312562 A1* | 12/2008 | Routh | .................. | A61B 8/4227 |
| | | | | 601/2 |
| 2009/0299239 A1* | 12/2009 | Meyer | .................... | A61H 11/00 |
| | | | | 601/149 |
| 2010/0016759 A1* | 1/2010 | Lavoisier | ............... | A61B 5/486 |
| | | | | 600/587 |
| 2010/0324429 A1* | 12/2010 | Leschinsky | ........ | A61B 5/02233 |
| | | | | 600/499 |
| 2014/0012120 A1* | 1/2014 | Cohen | ................ | A61B 5/02042 |
| | | | | 600/371 |
| 2015/0272452 A1* | 10/2015 | Mullin | ............... | A61B 5/02233 |
| | | | | 600/301 |
| 2015/0305958 A1* | 10/2015 | Hoff | ................... | A61B 17/1325 |
| | | | | 601/134 |
| 2017/0150972 A1* | 6/2017 | Kruk | ............... | A61B 17/1322 |
| 2017/0181921 A1* | 6/2017 | Wren | ..................... | A61H 11/00 |
| 2017/0312165 A1* | 11/2017 | Johnson | ................ | A61B 5/021 |
| 2021/0177432 A1* | 6/2021 | Rapp | ............... | A61B 17/1355 |
| 2022/0015652 A1* | 1/2022 | Lee | .................... | A61B 5/02233 |
| 2022/0240945 A1* | 8/2022 | Quinn | ................ | A61B 17/1327 |
| 2022/0346717 A1* | 11/2022 | Nguyen | .................. | A61B 5/01 |
| 2023/0012280 A1* | 1/2023 | Hoffman | .............. | A61B 17/135 |

\* cited by examiner

TOURNIQUET ASSEMBLIES AND SYSTEMS, AND METHODS FOR CONTROLLING TOURNIQUETS

FIELD OF THE INVENTION

The present invention relates to tourniquet assemblies and systems, and methods for controlling tourniquets and similar devices for restricting blood flow in a body part, and in particular to such devices operated by inflation using a pressurised fluid such as air.

BACKGROUND OF THE INVENTION

Tourniquets used in surgery are designed to occlude blood flow to a body part (most usually a limb) during the surgical procedure. They are also used in emergency trauma situations to reduce blood loss from a traumatic injury.

Tourniquets can be manually inflated, or can be inflated under the control of an automated controller. For conventional automated tourniquets the surgeon or operator determines what pressure is required in the tourniquet and then the electronic controller maintains this pressure in the tourniquet. There is also a category of tourniquets, such as in the present instance, known as smart tourniquets. A smart tourniquet makes a decision in firmware about the required tourniquet pressure based on an algorithm and based on sensor inputs. The electronic controller for a smart tourniquet (and indeed any automated tourniquet) may be integrated into the tourniquet, or may be an external controller.

The specification for a smart tourniquet is relatively simple—it should provide an occlusion to blood flow into a limb (that is an arm or a leg) during surgery in order to prevent bleeding (or if used for treating trauma in an emergency, it should provide an occlusion to prevent excessive blood loss). The means of occlusion is typically a pneumatically inflatable cuff fitted around the proximal end of the limb. The designation "smart" means that the pressure to which the cuff is inflated should be determined by some measurement of patient vital signs and thereby tailored to the patient rather than simply one-pressure-fits-all.

In contrast, non-smart tourniquets are merely inflated to an excess of pressure to which the patient systolic pressure is unlikely ever to reach and left at this pressure for the duration of the surgery. This approach ensures that there is no bleeding during the surgery but can lead to many post-operative complications, the least of which is bruising.

Systolic pressure is also known as "limb occlusive pressure (LOP)" in the context of the tourniquet and is defined as the pressure needed in the tourniquet in order to adequately occlude blood flow. It is well known however that LOP changes in the course of surgery; most commonly it reduces as a result of anaesthesia, so that even if tourniquet pressure is set at a reasonable pressure at the start of surgery when LOP is normal, this is no guarantee that it will not be excessive later in the surgical procedure when LOP may have dropped substantially.

Conventional smart tourniquets operate to maintain the tourniquet pressure at a set value, relative to the LOP occlusion pressure which is determined in advance of surgery in conventional fashion. This means that if the LOP drops or increases then the pressure may be excessive leading to tissue damage and post-operative pain, or alternatively it may be too low resulting in the tourniquet being ineffective to occlude flow to the surgical site.

SUMMARY OF THE INVENTION

In accordance with one aspect of the invention there is provided a method of controlling a tourniquet comprising the steps of:
  (a) providing an inflatable tourniquet on a limb together with a proximal strain gauge positioned on the limb proximally of the tourniquet and a distal strain gauge positioned on the limb distally of the tourniquet, wherein the proximal and distal strain gauges provide respective output signals indicative of volumetric changes in the limb proximally of and distally of the tourniquet, respectively;
  (b) inflating the tourniquet to a working pressure which exceeds the limb occlusion pressure (LOP) of said body part, such that the distal strain gauge output signal is indicative of a constant volume;
  (c) determining, from the proximal strain gauge output, a characteristic of the time-varying volumetric changes in the proximal limb volume; and
  (d) responsive to a change in said characteristic indicative of a reduction in the time-varying volumetric changes in the proximal limb volume, reducing the working pressure in the tourniquet.

Surprisingly it has been confirmed that changes in limb occlusion pressure, in a totally occluded limb, are observable using only a proximal strain gauge. Therefore, monitoring the volumetric changes in the limb above a fully occluding tourniquet provides a useful signal that a variation in the working pressure of the tourniquet is justified or advisable. This allows an automated smart controller to safely reduce tourniquet pressure without risking the flow of blood past the tourniquet (which might be dangerous when the tourniquet is used as an emergency treatment, and would be extremely disadvantageous e.g. during surgery if arterial blood flow unexpectedly appeared).

Preferably, the method further comprises the step of:
  responsive to a signal from the distal strain gauge indicating the onset of volumetric changes in the distal limb volume while the tourniquet is inflated, increasing the working pressure in the tourniquet.

Such a signal is an important safety consideration. Any reliably observed time-varying signal distal of the tourniquet indicates the onset of blood flow.

Preferably, step (b) of inflating the tourniquet to a working pressure comprises increasing the inflation pressure within the tourniquet until the output signal from the distal strain gauge shows a constant distal limb volume.

Preferably, the method further comprises monitoring the time-varying pressure induced in the inflated tourniquet by the vascular system of the portion of the limb beneath the tourniquet.

The observation of changes in the time-varying induced pressure provides a further useful signal to enable reliable and improved control of the tourniquet pressure. In particular, time-varying changes which are synchronised with the time-varying signal from the proximal strain gauge, may confirm that LOP has changed and that a variation in the tourniquet pressure is required or advised.

Preferably, the method further comprises determining a periodic measurement characteristic from the time-varying pressure induced in the inflated tourniquet, and determining whether an output signal from the distal strain gauge exhibits time variations corresponding to said periodic measurement characteristic, and if so, increasing the working pressure in the tourniquet.

Preferably, the method further comprises determining a periodic measurement characteristic from the time-varying pressure induced in the inflated tourniquet, and wherein said characteristic of the time-varying volumetric changes in the proximal limb volume comprise a measurement of the synchronicity of the time-varying signal from the proximal strain gauge with said periodic measurement characteristic.

There is also provided a tourniquet assembly comprising:
(a) an inflatable tourniquet;
(b) a proximal strain gauge disposed adjacent the tourniquet for encircling a limb to which the tourniquet is applied, the proximal strain gauge being disposed relative to the tourniquet such that when the tourniquet is applied to a limb the proximal strain gauge is positioned on the limb proximally of the tourniquet; and
(c) a distal strain gauge disposed adjacent the tourniquet for encircling a limb to which the tourniquet is applied, the distal strain gauge being disposed relative to the tourniquet such that when the tourniquet is applied to a limb the distal strain gauge is positioned on the limb distally of the tourniquet.

Preferably, one or both strain gauge(s) is/are integrated into the tourniquet by being mounted on the internal surface of the tourniquet to be in contact with a limb to which the tourniquet is applied.

Alternatively, the strain gauges may be provided as separate components to be applied to the limb under or adjacent the tourniquet in use.

There is further provided a tourniquet system comprising:
(a) an inflatable tourniquet as defined above;
(b) an inflation system for controllably inflating and deflating the tourniquet;
(c) a controller which receives respective output signals from the proximal and distal strain gauges which are indicative of volumetric changes in the limb proximally of and distally of the tourniquet, respectively;
wherein the controller is programmed to:
inflate the tourniquet to a working pressure which exceeds the limb occlusion pressure (LOP) of said body part, such that the distal strain gauge output signal is indicative of a constant volume;
(ii) determine, from the proximal strain gauge output, a characteristic of the time-varying volumetric changes in the proximal limb volume; and
(iii) responsive to a change in said characteristic indicative of a reduction in the time-varying volumetric changes in the proximal limb volume, reduce the pressure in the tourniquet.

The controller may be programmed further to carry out any additional steps of the methods recited above or disclosed below.

BRIEF DESCRIPTION OF THE DRAWINGS

The invention will now be further illustrated by the following description of embodiments thereof, given by way of example only with reference to the accompanying drawings, in which.

DETAILED DESCRIPTION OF PREFERRED EMBODIMENTS

Figure 1:
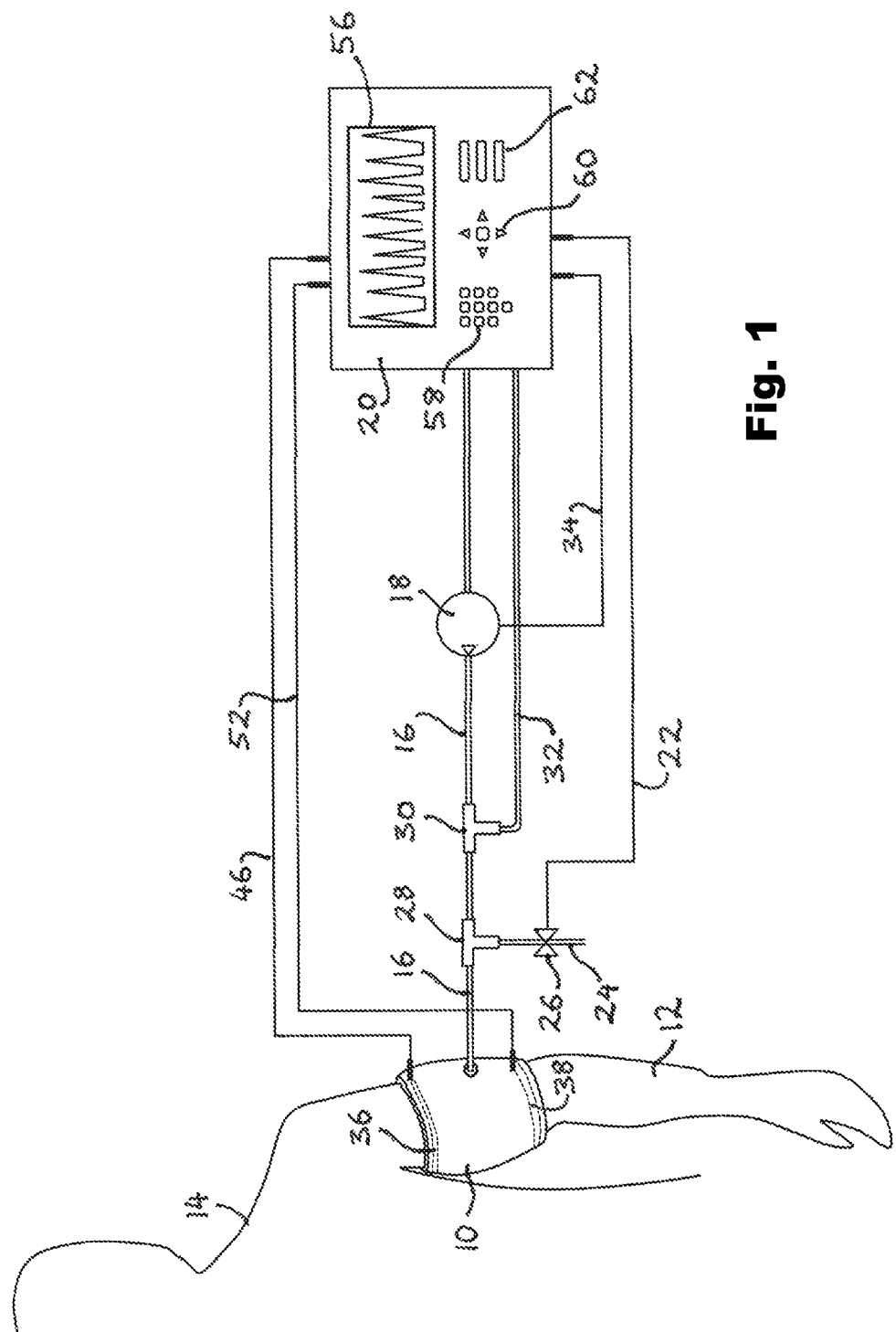
FIG. 1 is a schematic diagram of a system according to the invention.

In FIG. 1 there is shown a tourniquet 10 applied to an arm 12 of a subject 14. The tourniquet 10 is controllably inflated or deflated via an inflation tube 16 connected to a pump 18 which in turn is controlled by a control unit 20. As indicated above, while the control unit is shown here as a separate component, some or all of its functionality may be integrated into the tourniquet itself to provide a self-contained unit. However, for ease of description herein, the various components are shown as discrete, connected units.

The tourniquet can be controllably deflated through an exhaust tube 24 to which is fitted an electronically controlled variable valve 26 which can be proportionally controlled between a fully open state and a fully closed state under the control of electrical signals generated by the control unit and carried to the valve 26 by a respective electrical lead 22. The exhaust tube is connected to the inflation tube 16 via a T-piece 28.

The pressure in the tourniquet 10 is monitored by a pressure sensor (not shown) within the control unit which is in communication with the pressure in the inflation tube (and therefore the tourniquet also) via a T-piece connector 30 and a pressure sensor tube 32 leading to the control unit 20.

The pump 18 is operated by the control unit to control the inflation pressure of the tourniquet, with control signals carried via a respective electrical lead 34. By monitoring the pressure observed in pressure sensor tube 32, the control unit may operate the pump 16 and exhaust valve 26 to maintain a desired tourniquet pressure, and may vary this over time to affect the flow of blood beyond the tourniquet into the limb to which it is fitted. A dump valve (not shown) may also be fitted for rapid deflation of the tourniquet, and a safety valve may be fitted to prevent the tourniquet pressure from exceeding safe limits.

Figure 2:
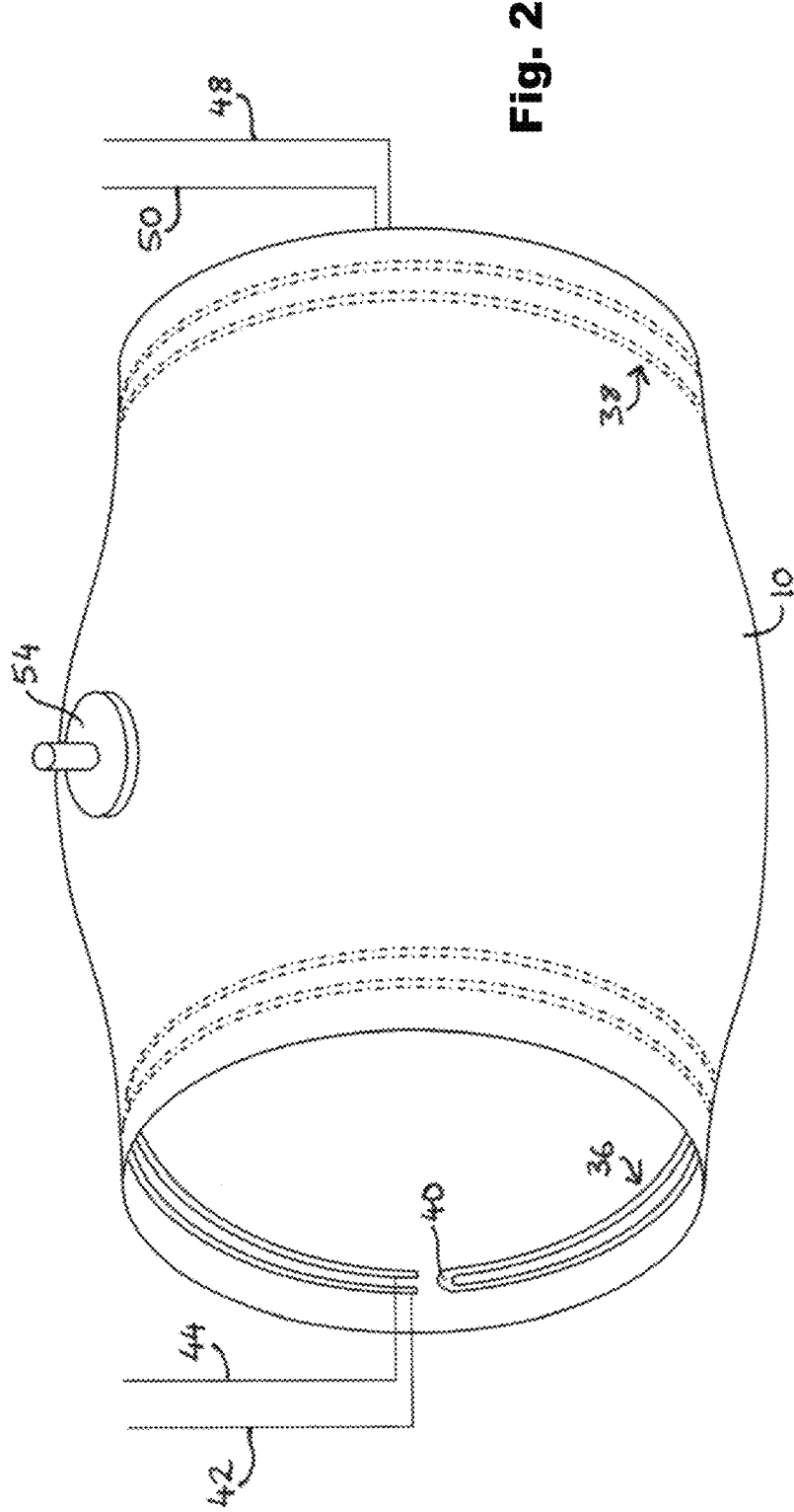
FIG. 2 is a perspective view of a tourniquet assembly according to the invention.

Referring additionally to FIG. 2, the inner surface of the tourniquet in contact with the subject's limb carries a pair of strain gauges 36 and 38. The strain gauge 36 visible within the tourniquet in FIG. 2 is located at the proximal (i.e. closer to the heart) end of the tourniquet while the strain gauge band 38, which is shown in broken outline as it is concealed within the tourniquet, is located at the distal end. The inflatable chamber of the tourniquet, which applies pressure to the limb it encircles, is between the two strain gauges 36, 38.

Referring in particular to strain gauge 36 (it being understood that strain gauge 38 is identical), this takes the form of a thin-walled Silastic tubing of 1 mm external diameter, filled with an Indium-Gallium alloy and which is capped at either end with machined metal plugs ("Silastic" is a trade mark of Dow Corning, referring to an elastically deformable silicone elastomer). The tubing is doubled back on itself at the midpoint 40, with the terminal ends of the tubing each connected to a respective electrical connection 42, 44.

The length of the tubing is chosen to ensure that it is elastically deformed when the tourniquet is fitted to a limb (for this reason, different size tourniquets may be provided for different patients and different limbs, or for upper and lower limbs, etc.). As the tubing stretches it changes the shape of the column of conductive indium gallium and thereby changes its resistance.

In reality the electrical connections to the tubing may be slightly more complex. For example, while each of the electrical connections 42, 44 is shown as a single connection, each preferably has two wires soldered to the end of the strain gauge to which it is attached. This allows current to be injected on one wire of the connection and voltage can be measured using the other wire at each end. This arrangement means that the impedance of the wire does not contribute to the result and only the impedance of the strain gauge is measured back at the control unit. The four wires (two for each connection) are carried in a single cable, shown in FIG. 1 as cable 46.

Similarly, the distal strain gauge has two connections 48, 50, each having two wires, and all carried in a cable 52 (FIG. 1).

Finally, in FIG. 2 there is visible the pneumatic connection 54 to which the inflation tube 16 (FIG. 1) attaches, permitting the controlled inflation and deflation of the tourniquet chamber.

Increases in the volume of the limb underlying the proximal strain gauge 36 are translated into increasing output signals while decreases are translated into decreasing output signals. Similar signals are generated by the distal strain gauge 38 arising from changes in the volume of the portion of the limb underlying the distal strain gauge. As a portion of the limb becomes engorged with blood the strain gauge signal will increase. If there is a pulse within the portion of the limb a time-varying signal will be observed as the limb momentarily increases in volume and decreases in volume in line with the flow of blood through that limb portion. In some cases, there is no capacity in the vascular (venous) system for the temporary engorgement to be dispersed. In those cases, the pulses of blood into the limb segment may not exhibit any decrease in volume, and it has been observed that the limb segment volume may simply step up incrementally from pulse to pulse until it reaches a plateau where it cannot increase any further.

In addition, if there is arterial blood flow beneath the tourniquet's inflated chamber, there will be an induced pressure pulse in the tourniquet which will be communicated back through the inflation tube 16 and will be observable as a time-varying pressure fluctuation in the pressure sensor tube 32 (FIG. 1).

Referring back to FIG. 1, the control unit, described further below, is provided with a display 56, a keypad 58 for providing numeric inputs, and a number of control buttons 60 such as four-way directional arrows 60 and further buttons 62 (such as power, confirm and cancel buttons). Using the inputs, and responsive to prompts on the display, a user may control and program the operation of the control unit. When a tourniquet is connected and applied to a patient the display may also provide visual feedback on the system e.g. by displaying output signals from one of the strain gauges or the pressure sensor, or by displaying inferred or calculated information such as vital signs determined from these input signals or from other attached sensors.

Although the tourniquet assembly of FIG. 2 has the strain gauges integrated into the tourniquet, the scope of the claims extends also to a tourniquet having separate strain gauges which are assembled in use to provide one strain gauge proximal of the tourniquet and one distal of the tourniquet.

Figure 3:
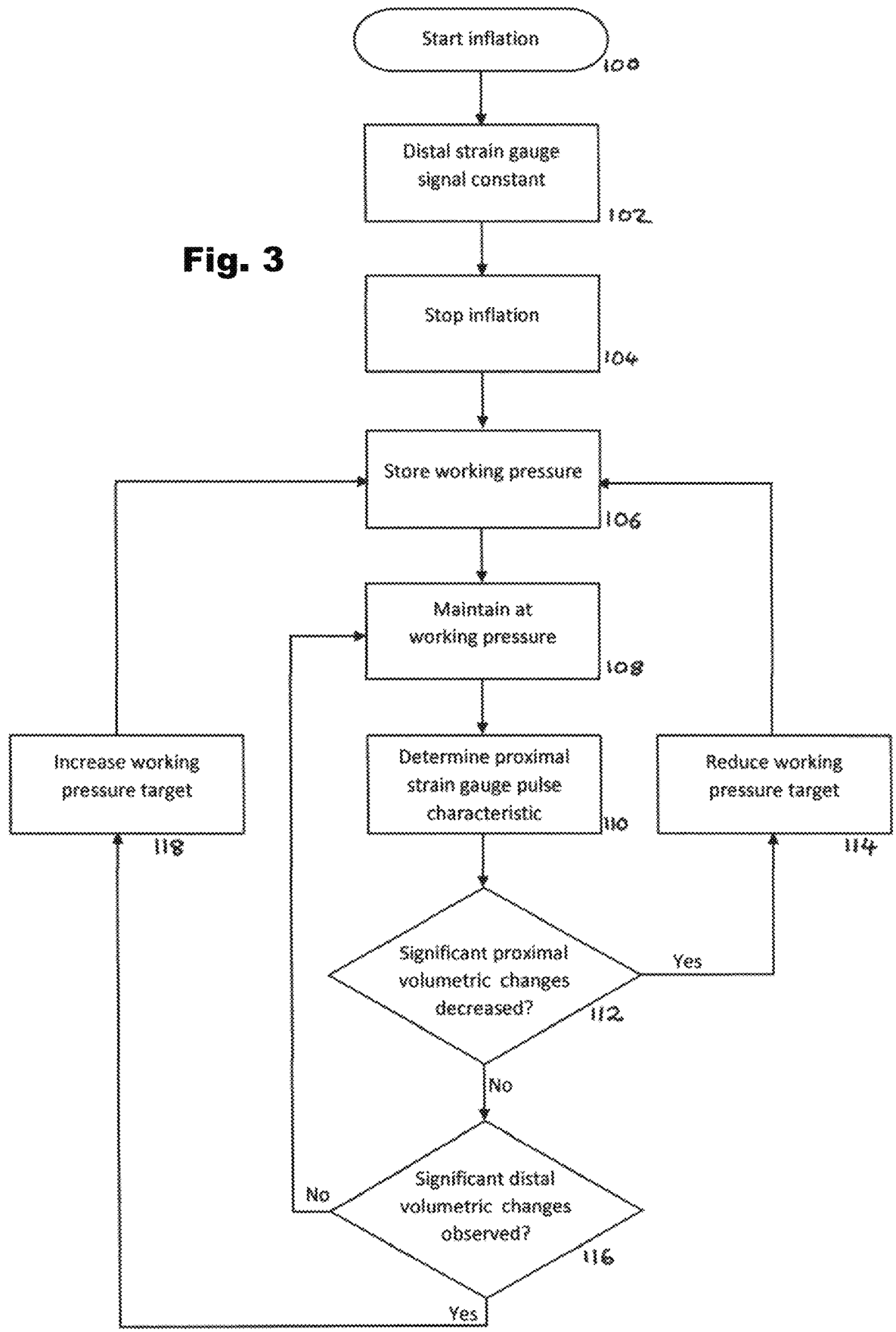
FIG. 3 is a flowchart of a method of controlling a tourniquet according to the invention.

FIG. 3 is a flowchart of a method of operation of the system shown in FIG. 1. In step 100, the pump starts to inflate the tourniquet. Prior to inflation and while the tourniquet pressure is less than the LOP, there will be a pulse in the distal part of the limb beyond the tourniquet, which will be observable as a time-varying signal from the distal strain gauge.

In step 102, the distal strain gauge signal is observed to be constant, indicating that there is no longer a pulse causing the distal limb portion to change volumetrically. This is a reliable signal that LOP has been reached and bloodflow to the distal portion of the limb is fully occluded. In step 104 the control unit signals the pump to stop inflating in response to the indication from the distal strain gauge.

The working pressure of the tourniquet is stored in step 106, and in step 108 the control unit controls the pump to maintain the tourniquet at the stored working pressure.

With the bloodflow past the tourniquet occluded, the proximal strain gauge signal is monitored to determine a pulse characteristic from the proximal strain gauge, step 110. As described further below, the observed signal will increase and decrease in time with the arterial pulse, as the proximal limb momentarily expands and contracts in time with the pulse. The characteristic may for example be the peak-to-trough pulse height, or a moving average of pulse heights, or some other smoothed measure such as the mean or median signal level over a number of pulse cycles. Each of these signals is observed to be responsive to changes in LOP, as described further below. In particular if a reduction in pulse height is observed, this may be a signal that the LOP has decreased so that the subject will benefit from a carefully controlled decrease in tourniquet pressure.

Accordingly, in step 112, a determination is made whether a significant change in the proximal limb time-varying volumetric measurement has been observed. The term "significant" refers to an observed change that is determined to be meaningful rather than simply meaning large in magnitude. As explained further below, the significance of an observed change can be determined from the proximal strain gauge signal alone, or from a correlation with other signals, in particular with the signal from the tourniquet pressure sensor.

If a change is determined to be significant and indicative that the LOP has decreased, then in step 114, the working pressure target is decreased, typically by a small amount to avoid the pressure in the tourniquet being lowered below the required pressure to occlude bloodflow to the distal limb. The reduced working pressure is stored, step 106, and the process continues as before with the tourniquet pressure adjusted accordingly.

In step 116, when a significant change in the distal limb volumetric measurement signalled from the distal strain gauge has been observed, this will typically be an indication that there is a resumption of bloodflow into the distal limb. Again "significant" means meaningful. Not every change or fluctuation in the signal from the distal gauge will indicate the onset of bloodflow, so that the signal will be analysed either on its own or in conjunction with a signal from another sensor, in particular the pressure sensor in the tourniquet, to determine if corrective action needs to be taken.

If a change from the distal strain gauge is determined to be significant, and indicative that LOP has increased beyond the working pressure of the tourniquet, then in step 118 the working pressure target value is increased, and this is stored in step 106 with the process continuing by the pump increasing pressure to maintain the tourniquet at the new, higher, working pressure, step 108.

Figure 4:
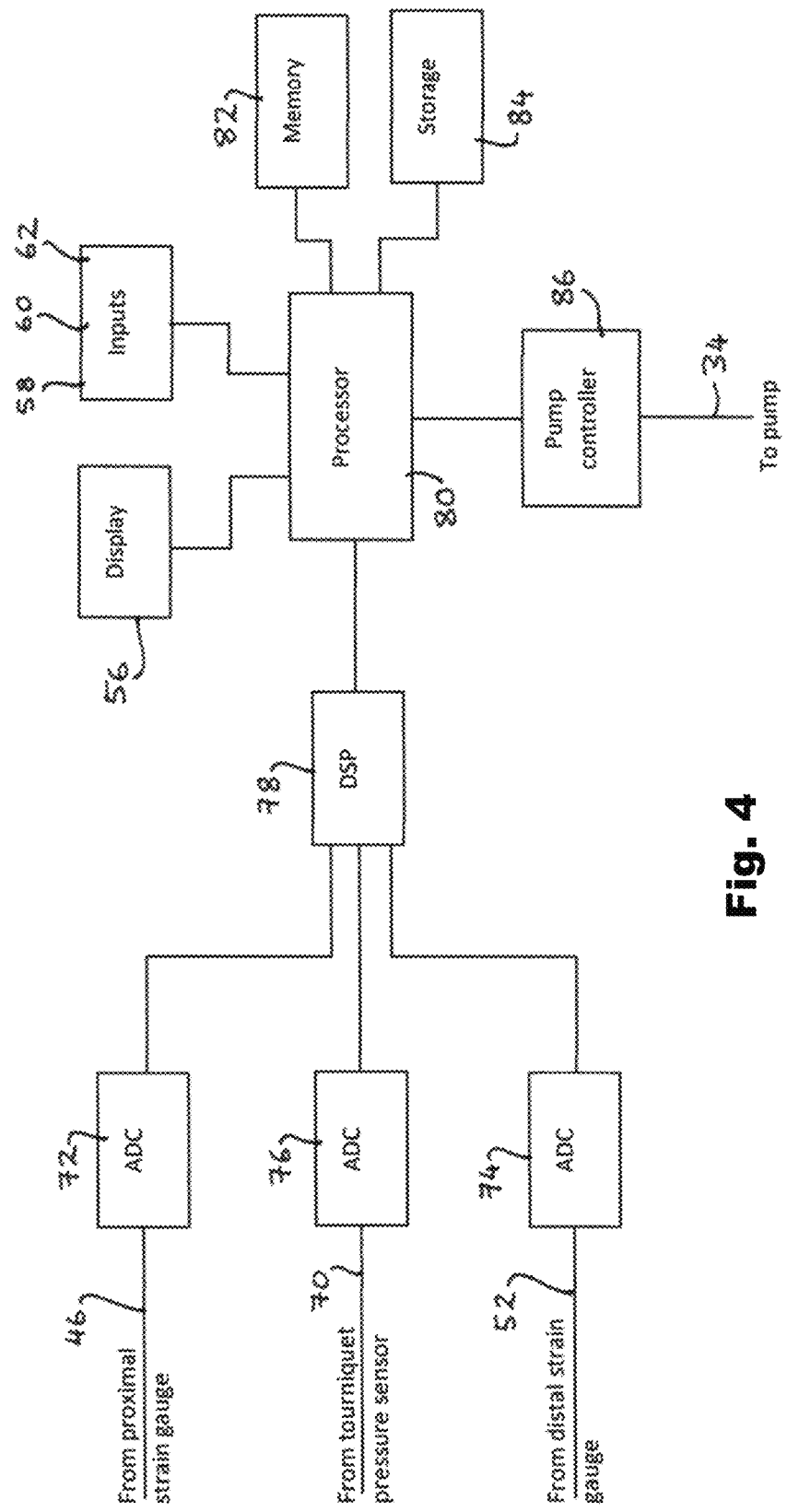
FIG. 4 is a block diagram of the controller of the system of FIG. 1.

FIG. 4 is a block diagram of the main functional components of the control unit 20 (FIG. 1). Signals are received via the connections 46, 52 from the proximal strain gauge and distal strain gauge and a further internal connection 70 from the pressure sensor. These analog signals are each processed by a respective digital-to-analog converter (DAC) 72, 74, 76, and the digitised signals are passed to a digital signal processor (DSP) 78 which extracts signal characteristics such as pulse height, pulse shape and pulse period. The signal characteristics are passed to a processor 80 which determines the action to take on the basis of the input signals and the programming of the processor. The processor may for example be programmed to perform the exemplary method of FIG. 3, or variations on this method described further below, or some other method falling within the teaching of this disclosure and the claims appended hereto. While the DSP is shown as a discrete component, the processor firmware may be programmed with signal processing capabilities.

The processor communicates (via suitable drivers in known manner) with the display 56 and the various input buttons 58, 60, 62 to provide output to a user and obtain inputs from the user. It will be appreciated that a wide range of technologies may be used to communicate with a control unit or other programmed system implementing the methods taught herein, and the particular hardware description provided here is by way of just one example. In accordance with conventional knowledge of computing systems, the processor is also provided with access to a working memory 82 and is in communication with storage 84 (such as a disk drive, read-only memory, flash memory, etc.) in which program instructions, operating system instructions, and working parameters can be stored and retrieved. The processor is also in communication with a pump controller 86 (or implements a pump controller programmatically itself) and provides pump control signals via the previously described electrical connection 34 to the pump. The processor or the pump controller may also provide deflation signals to the valve 26 (FIG. 1) via the electrical connection 22 to the valve.

While the connections shown here are indicated as hard-wired connections, it will be appreciated that any or all of the connections can be implemented wirelessly, including in particular the connections to the tourniquet and the associated sensors, and the connection to the pump.

Figure 5:
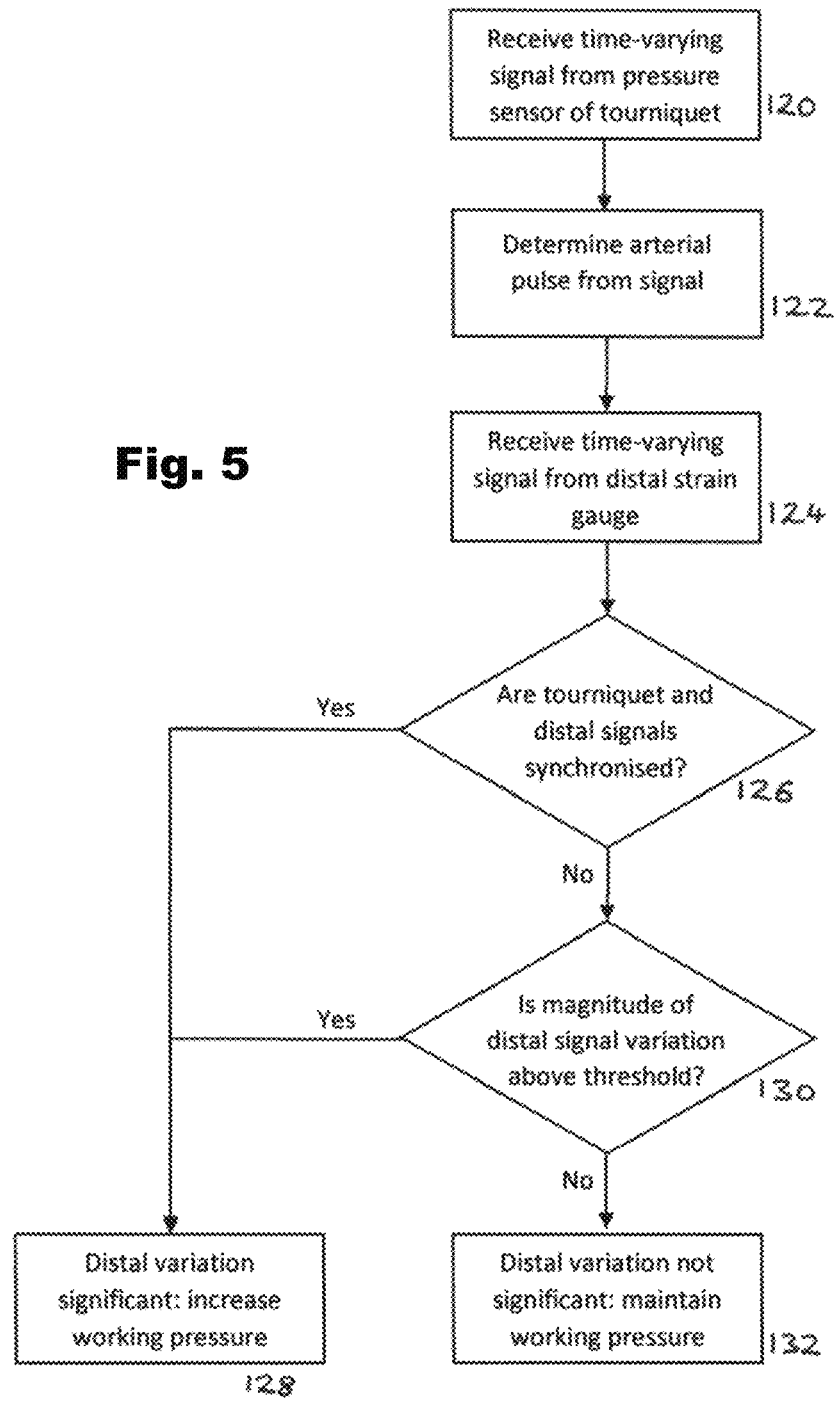
FIG. 5 is a flowchart of a variation on the method of FIG. 3.

FIG. 5 is a flowchart of a refinement of the method for determining whether a change in signals from the distal strain gauge is considered significant. During operation of the method of FIG. 3, time varying signals from the pressure sensor of the tourniquet are received by the control unit, step 120. The DSP extracts signal characteristics, and the processor derives from these an arterial pulse signal, step 122. At some point, the processor notes that the distal strain gauge is providing a time-varying signal (rather than the static signal expected from a distal limb that has been fully occluded), step 124.

In step 126, a comparison between the time-varying characteristic of the distal strain gauge signal and the pressure sensor signal is carried out, to determine if they are synchronised in any way. The significance of observing a synchronised signal is that it strongly indicates that blood flow below the tourniquet has extended all the way past and into the distal limb portion. Conversely, a transient change in the signal from the distal strain gauge, or indeed a series of changes, which is/are not synchronised with the pulse characteristic of the induced pressure pulse in the tourniquet, is unlikely to be indicative of resumed bloodflow. Determination of whether the signals are synchronised can be performed in numerous ways using established pattern-matching techniques.

If the signals are determined to be synchronised then the distal variation is determined to be significant and the working pressure is increased, step 128.

If the signals do not appear to be synchronised in step 126, a further determination is made whether the magnitude of signal variation is above a threshold, step 130. For example, it may be decided that any periodic volumetric variation in the distal limb portion that is of a certain magnitude or that has a periodicity falling within the expected range of a patient's pulse rate, should be flagged as significant, even if it cannot be matched against the signal from the pressure sensor. If the determination in step 130 is positive, the working pressure is increased, step 128. If the determination in step 130 is negative, then it may be concluded that the distal variation was not significant and the current working pressure is maintained, step 132.

Figure 6:
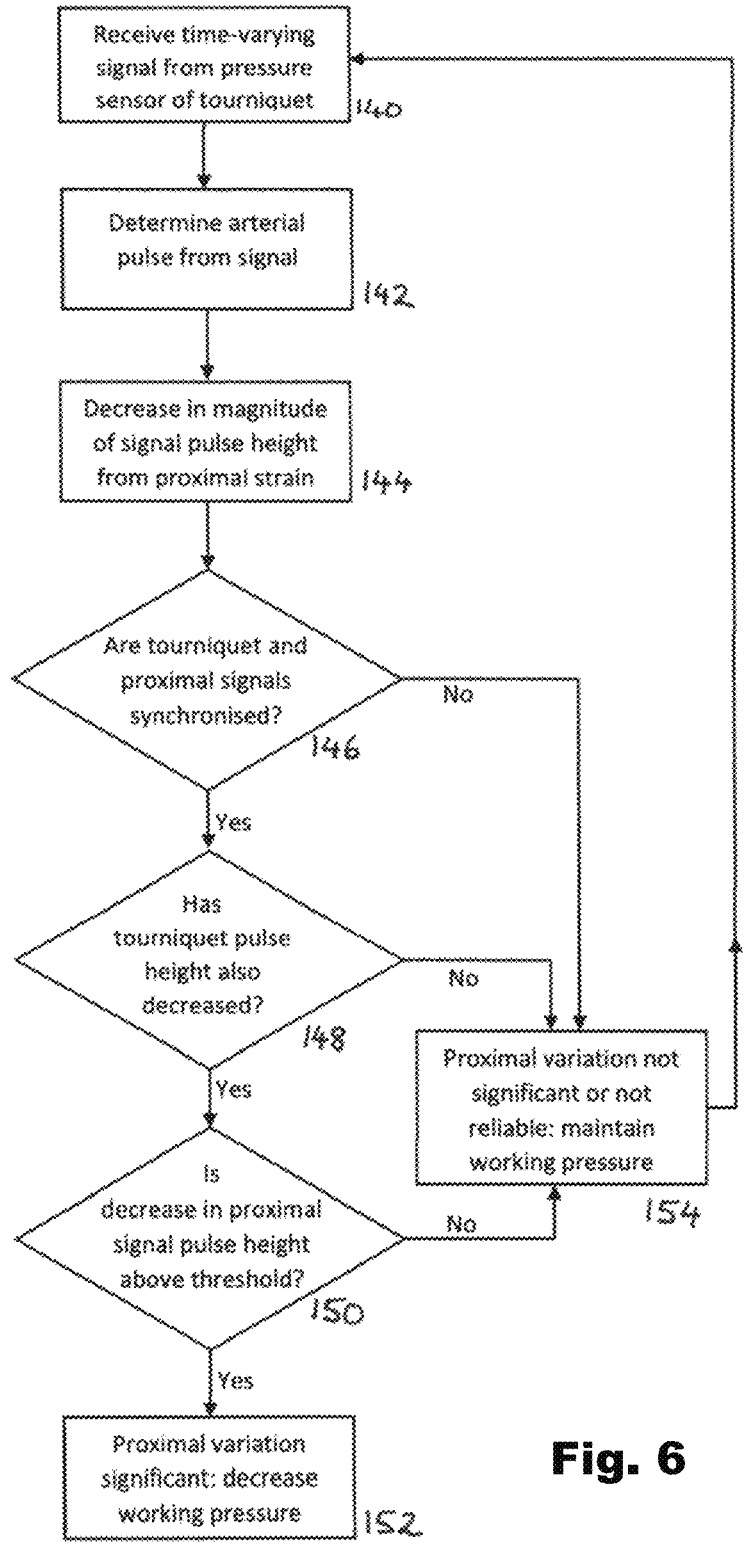
FIG. 6 is a flowchart of a further variation on the method of FIG. 3.

FIG. 6 is a flowchart of a refinement of the method for determining whether a change in signals from the distal strain gauge is considered significant. During operation of the method of FIG. 3 and as described also in relation to FIG. 5, time varying signals from the pressure sensor of the tourniquet are received by the control unit, step 140. The DSP extracts signal characteristics, and the processor derives from these an arterial pulse signal, step 142. At some point, the processor notes that the magnitude of the signal pulses from the proximal strain gauge have decreased in magnitude, step 144.

This may be indicative that LOP has decreased, although care must be taken not to prematurely decrease the tourniquet pressure, so additional confirmation may be required that the change is significant. Thus in step 146 a determination is made as to whether the tourniquet pressure signal and the proximal strain gauge signal are synchronised. If so, a further check is made in step 148 whether the induced tourniquet pressure sensor signal pulse height has also decreased. Possibly further checks may be made that the magnitudes of the respective decreases from the two sensors are matched, for further assurance that the observed decreases are attributable to the same cause namely a decrease in LOP. If the determination in step 148 is positive, then finally it is verified in step 150 whether the decrease in the proximal signal pulse height is above a threshold that indicates that a sufficiently significant change has occurred to require a decrease in the working tourniquet pressure. If each of the determinations 146, 148 and 150 is positive, the conclusion is that the proximal limb time-varying volumetric change is significant and indicative of a decrease in LOP such that the tourniquet pressure may be safely reduced and should be reduced to prevent damage to the underlying tissue. Accordingly in step 152 the working pressure is decreased by a safe amount.

If any of the determinations in steps 146, 148 or 150 is negative, then it is determined in step 154 that the reduction in volumetric changes of the proximal limb are not significant or not reliable, so that working pressure should be maintained at the current level. For safety reasons, the system is programmed to require multiple positive determinations before decreasing tourniquet pressure. Following step 154, the process returns to step 140.

A set of experiments was carried out to verify if the proximal and distal strain gauges could distinguish changes in limb occlusion pressure, and thus provide a reliable basis for adjusting the working pressure in a smart tourniquet.

A tourniquet was fitted to the upper arm of a healthy subject. In all tests the arm was supported in a horizontal position at shoulder height. Before each test the arm was drained by asking the subject to raise their arm above their head for one minute. Then with the arm supported, the tourniquet was inflated to a working pressure of either 100 mm Hg or 200 mm Hg.

Test 1: Seated Subject, 100 mm Hg Working Pressure, Distal Strain Gauge Measurements The distal strain gauge showed a time varying signal, indicating that blood was flowing past the tourniquet. The signal was indicative of partial occlusion: the distal sensor exhibited an increasing limb volume with each pulse as it became engorged with blood due to arterial flow passing the tourniquet and venous flow being inhibited.

Figure 7:
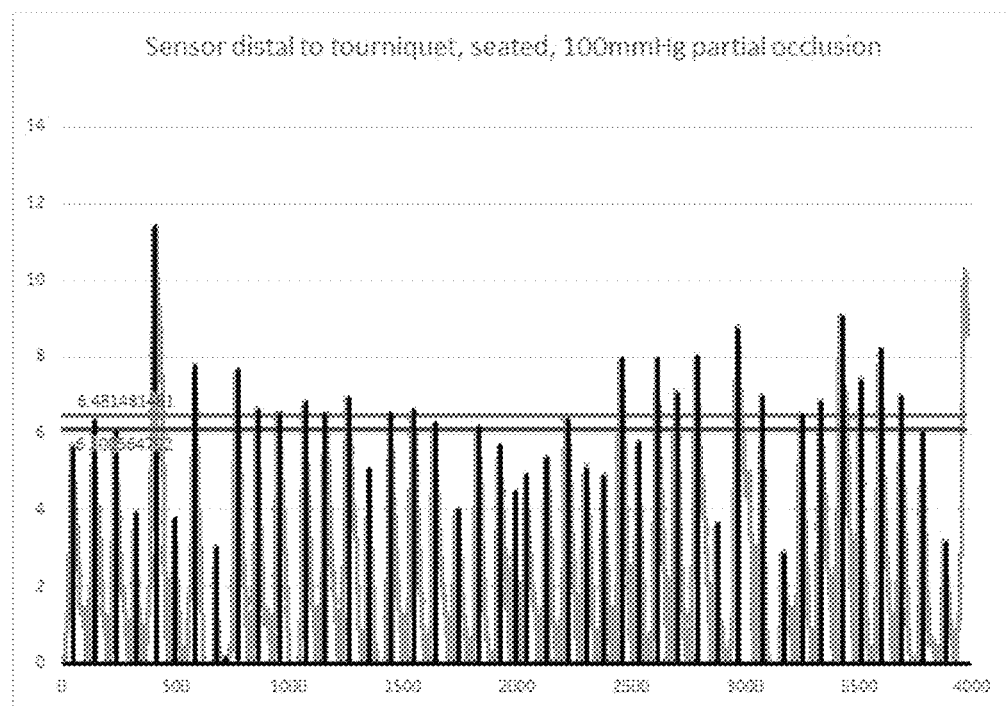
FIG. 7 is a plot of output signals from a distal strain gauge on a limb partially occluded by a tourniquet for a seated subject.

FIG. 7 is a trace of the output signal from the distal strain gauge, with values normalised to remove baseline variability. Baseline variability arises due to engorgement of the limb with blood over time. By normalising the signals, each peak shows the delta in signal attributable to each pulse. On the graph, the trace is shown in grey, with each peak indicated by a vertical black line. The two horizontal lines show the mean peak height and the median peak height, with the mean being below the median. The mean height was 6.100565 and the median was 6.481481.

Test 2: Standing Subject, 100 mm Hg Working Pressure, Distal Strain Gauge Measurements Then the test was repeated with the subject standing (after the tourniquet was removed and the arm had been drained for one minute). Again, partial occlusion was observed, with blood flow into the distal limb and a gradual engorgement.

Figure 8:
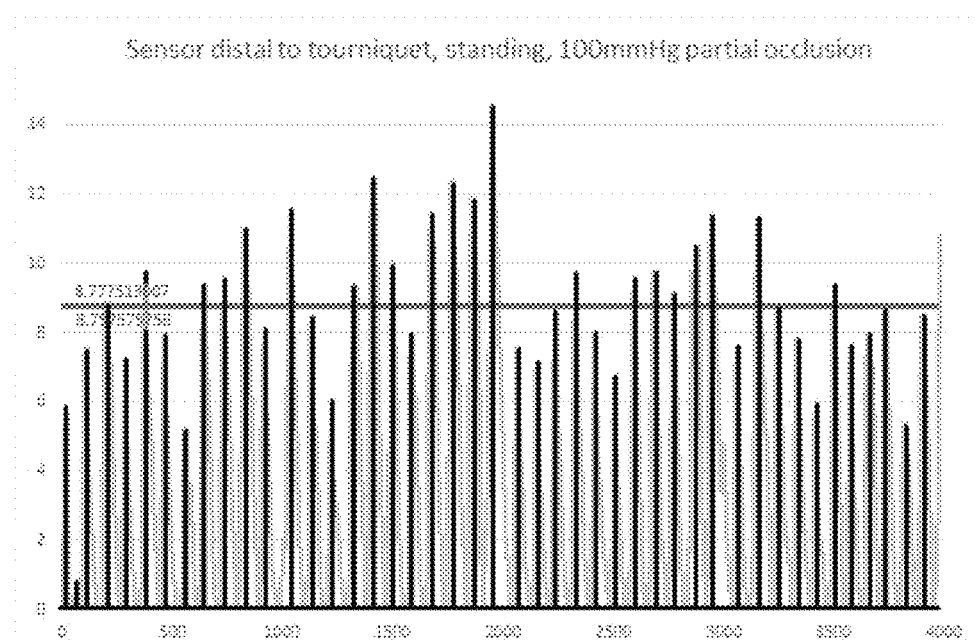
FIG. 8 is a plot of output signals from a distal strain gauge on a limb partially occluded by a tourniquet for a standing subject.

FIG. 8 is a trace of the output signal from the distal strain gauge for the second test. The mean and median height lines are effectively coincident on this plot, as the pulse mean height was 8.777513 and the median height 8.757576.

This increase in signal level at the distal strain gauge from a mean of approximately 6.10 units to 8.78 units clearly showed that the limb volume was expanding more on each pulse when standing than when seated. We do not claim from this (and nor is it necessary for the experimental design) that the blood pressure of the subject is greater when standing than when seated, though this probably is true. However it is absolutely clear from this data that a larger volume of blood was pumped past the 100 mmHg occlusion on each heartbeat when the subject was standing compared with when they were seated and therefore by inference a greater LOP applies when this subject is standing compared with when they are seated.

This further demonstrated that the distal strain gauge can be used to see when the tourniquet has insufficient pressure, as a pulse can be observed past the tourniquet.

With those conclusions established, the performance of the proximal strain gauge was evaluated under conditions of total occlusion (this being the desired state when a tourniquet is applied and operating correctly, i.e. where blood flow past the tourniquet is stopped entirely).

Test 3: Seated Subject, 200 mm Hg Working Pressure, Proximal Strain Gauge Measurements After again draining the arm, and with the subject seated, the tourniquet was inflated to 200 mm Hg, leading to total occlusion.

Figure 9:
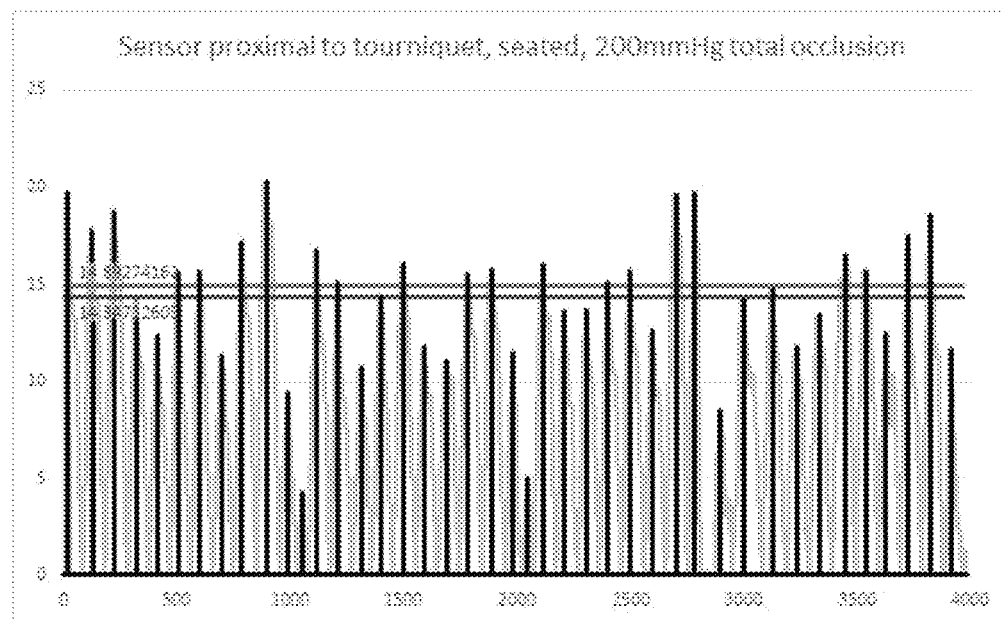
FIG. 9 is a plot of output signals from a proximal strain gauge on a limb fully occluded by a tourniquet for a seated subject.

The proximal strain gauge sensor readings were plotted, and the results are shown in FIG. 9. The mean value for pulse peak height was 14.34713, while the median was 14.89274.

With this established, the next test was designed to investigate the effects observable at the proximal strain gauge when LOP increases, knowing that repeating the test with the subject standing would cause an increase in LOP.

Test 4: Standing Subject, 200 mm Hg Working Pressure, Proximal Strain Gauge Measurements After again draining the arm, and with the subject standing, the tourniquet was inflated to 200 mm Hg, leading to total occlusion.

Figure 10:
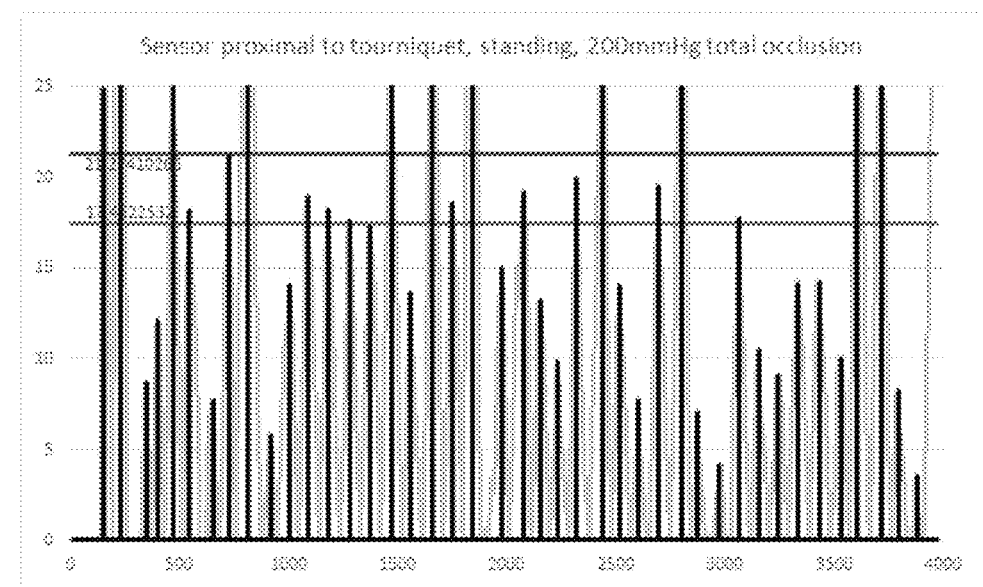
FIG. 10 is a plot of output signals from a proximal strain gauge on a limb fully occluded by a tourniquet for a standing subject.

The proximal strain gauge sensor readings were plotted, and the results are shown in FIG. 10. The horizontal mean line is uppermost in this plot with the mean value of pulse peak height at 21.2741, while the median was 17.45225.

Taken together the four tests provide a clear confirmation that the proximal strain gauge can provide a measure of changes in LOP, even for a fully occluded limb. Observing a decrease in pulse peak heights at the proximal strain gauge, even while the limb remains fully occluded, provides a reliable indication that LOP has decreased, and vice versa. Thus the tourniquet pressure may be lowered, preferably subject to additional safeguards (such as seeking a corresponding change in induced tourniquet pressure), without risking blood flow past the tourniquet. In this way, the smart tourniquet may be operated to vary the working pressure of the tourniquet in response to changes in the measured output of the proximal strain gauge.

The invention is not limited to the specific embodiments herein which may be varied within the scope of the appended claims.

The invention claimed is:

1. A method of controlling a tourniquet comprising the steps of:
    (a) providing an inflatable tourniquet on a limb together with a proximal strain gauge positioned on the limb proximally of the tourniquet and a distal strain gauge positioned on the limb distally of the tourniquet, wherein the proximal and distal strain gauges provide respective output signals indicative of volumetric changes in the limb proximally of and distally of the tourniquet, respectively;
    (b) inflating the tourniquet to a working pressure which exceeds the limb occlusion pressure (LOP) of said body part, such that the distal strain gauge output signal is indicative of a constant volume;
    (c) determining, from the proximal strain gauge output, a characteristic of the time-varying volumetric changes in the proximal limb volume; and
    (d) responsive to a change in said characteristic indicative of a reduction in the time-varying volumetric changes in the proximal limb volume, reducing the working pressure in the tourniquet by an amount which reduces pressure on the limb while remaining above the limb occlusion pressure.

2. A method according to claim 1, further comprising the step of:
    responsive to a signal from the distal strain gauge indicating the onset of volumetric changes in the distal limb volume while the tourniquet is inflated, increasing the working pressure in the tourniquet.

3. A method according to claim 1, wherein step (b) of inflating the tourniquet to a working pressure comprises increasing the inflation pressure within the tourniquet until the output signal from the distal strain gauge shows a constant distal limb volume.

4. A method according to any preceding claim, further comprising monitoring the time-varying pressure induced in the inflated tourniquet by the vascular system of the portion of the limb beneath the tourniquet.

5. A method according to claim 4, further comprising determining a periodic measurement characteristic from the time-varying pressure induced in the inflated tourniquet, and determining whether an output signal from the distal strain gauge exhibits time variations corresponding to said periodic measurement characteristic, and if so, increasing the working pressure in the tourniquet.

6. A method according to claim 4, further comprising determining a periodic measurement characteristic from the time-varying pressure induced in the inflated tourniquet, and wherein said characteristic of the time-varying volumetric changes in the proximal limb volume comprise a measurement of the synchronicity of the time-varying signal from the proximal strain gauge with said periodic measurement characteristic.

* * * * *